US009633430B2

(12) United States Patent
Fan

(10) Patent No.: US 9,633,430 B2
(45) Date of Patent: Apr. 25, 2017

(54) METHOD FOR ANALYZING FUNCTIONAL MRI BRAIN IMAGES

(75) Inventor: Yong Fan, Beijing (CN)

(73) Assignee: INSTITUTE OF AUTOMATION, CHINESE ACADEMY OF SCIENCES, Beijing (CN)

(*) Notice: Subject to any disclaimer, the term of this patent is extended or adjusted under 35 U.S.C. 154(b) by 314 days.

(21) Appl. No.: 14/374,853

(22) PCT Filed: Dec. 28, 2011

(86) PCT No.: PCT/CN2011/084825
§ 371 (c)(1),
(2), (4) Date: Mar. 11, 2015

(87) PCT Pub. No.: WO2013/097118
PCT Pub. Date: Jul. 4, 2013

(65) Prior Publication Data
US 2015/0243023 A1 Aug. 27, 2015

(51) Int. Cl.
G06T 7/00 (2006.01)
G06K 9/62 (2006.01)
(Continued)

(52) U.S. Cl.
CPC .......... G06T 7/0012 (2013.01); A61B 5/055 (2013.01); G01R 33/4806 (2013.01);
(Continued)

(58) Field of Classification Search
CPC ........ G06T 7/0012; G06T 2207/10088; G06T 2207/20076; G06T 2207/20081;
(Continued)

(56) References Cited

U.S. PATENT DOCUMENTS 7,720,267 B2 5/2010 Fuchs
2009/0124886 A1 5/2009 Wang et al.
2010/0074499 A1* 3/2010 Wels .................... G06T 7/0081
382/131

FOREIGN PATENT DOCUMENTS

CN 1775172 A 5/2006
CN 101061951 A 10/2007
(Continued)

OTHER PUBLICATIONS

Pekar, James, and Vince Calhoun. "Spatial & Temporal Independent Component Analysis of fMRI Data with Two Task-Related Waveforms." University of Maryland (Feb. 20, 2006): 1. Accessed Aug. 5, 2016. http://www.nrc-iol.org/cores/mialab/personnel/calhoun/2001_ISMRM_SICATICA.pdf.*
(Continued)

Primary Examiner — Siamak Harandi
Assistant Examiner — Kate R Duffy
(74) Attorney, Agent, or Firm — Schwegman Lundberg & Woessner, P.A.

(57) ABSTRACT

A method for analyzing fMRI brain data, comprising: collecting the fMRI data including spatial information and temporal information from subjects; preprocessing the fMRI data; computing independent components (ICs) and their corresponding time course for each individual subjects; constructing an initial functional connectivity pattern; constructing a classifier based on the functional connectivity pattern; and applying the classifier to functional connectivity patterns of individual subjects for statistical analysis or diagnosis. The method may be used in fMRI based studies of a brain function and brain disorder diagnosis.

9 Claims, 3 Drawing Sheets

(51) Int. Cl.
*G01R 33/48* (2006.01)
*A61B 5/055* (2006.01)

(52) U.S. Cl.
CPC ...... *G06K 9/6267* (2013.01); *A61B 2576/026* (2013.01); *G06K 9/624* (2013.01); *G06K 2209/25* (2013.01); *G06T 2207/10076* (2013.01); *G06T 2207/10088* (2013.01); *G06T 2207/20076* (2013.01); *G06T 2207/20081* (2013.01); *G06T 2207/30016* (2013.01)

(58) Field of Classification Search
CPC . G06T 2207/30016; G06T 2207/10076; A61B 2576/026; G06K 2209/25; G06K 9/624
See application file for complete search history.

(56) References Cited

FOREIGN PATENT DOCUMENTS

| | | |
|---|---|---|
| CN | 101292871 A | 10/2008 |
| CN | 101502413 A | 8/2009 |
| CN | 101912263 A | 12/2010 |
| WO | WO-2005/101298 A2 | 10/2005 |
| WO | WO-2013/097118 A1 | 7/2013 |

OTHER PUBLICATIONS

Fan, Youn. "Discriminant Analysis of Resting-State Functional Connectivity Patterns on the Grassmann Manifold." Proceedings of SPIE—The International Society for Optical Engineering 7623 (Mar. 2010): 1. Accessed Aug. 5, 2016. http://dx.doi.org/10.1117/12.844495.*

"International Application Serial No. PCT/CN2011/084825, International Preliminary Report on Patentability dated Jul. 1, 2014", 10 pgs.

"International Application Serial No. PCT/CN2011/084825, International Search Report mailed Sep. 13, 2012", (w/ English Abstract), 8 pgs.

"International Application Serial No. PCT/CN2011/084825, Written Opinion mailed Sep. 13, 2012", (w/ English Translation), 10 pgs.

Calhoun, Vince D., et al., "A review of group ICA for fMRI data and ICA for joint inference of imaging, genetic, and ERP data", *NeuroImage*, 45, (2009), S163-S172.

Fan, Yong, et al., "Discriminant analysis of functional connectivity patterns on Grassmann manifold", *NeuroImage*, 56, (2011), 2058-2067.

Smith, Stephen M., et al., "Advances in functional and structural MR image analysis and implementation as FSL", *NeuroImage*, 23, (2004), S208-S219.

* cited by examiner

METHOD FOR ANALYZING FUNCTIONAL MRI BRAIN IMAGES

PRIORITY APPLICATION

This application is a U.S. National Stage Filing under 35 U.S.C. 371 from International Application No. PCT/CN2011/084825, filed on 28 Dec. 2011, and published as WO 2013/097118 A1 on 4 Jul. 2013; which application and publication are incorporated herein by reference in their entirety.

TECHNICAL FIELD

This present invention generally relates to medical image processing, particularly to functional MRI (fMRI) brain image processing and analysis.

BACKGROUND

Functional magnetic resonance imaging (fMRI) as an imaging modality for recording the human brain activities with 4-dimensional (3-D space+1-D time) signals plays an increasingly important role in both basic and clinical research studies of the brain function. Based on the fMRI data collected at resting-state, the brain functional connectivity is typically investigated using regional correlation analysis based approaches or independent component analysis (ICA) methods. The former approaches estimate the brain connectivity by computing correlation measures of functional temporal signals between regions of interest (ROIs) or correlating functional temporal signals of a seed region to those of other brain voxels. The selection of ROIs typically requires a priori knowledge about a problem under study. In contrast to the regional correlation analysis methods, the ICA approach is a data driven technique. For brain network analysis, the ICA, particularly spatial ICA, is used to discover spatially independent components (ICs), each of which encodes temporally coherent brain regions. The temporally coherent brain regions encoded by each individual IC are often referred to as a functional network.

For ICA studies of multiple subjects, the spatial ICA is typically applied to concatenated group imaging data formed by concatenating imaging data from all subjects in the temporal dimension, and subject specific ICs are then obtained by back reconstruction or dual regression. In most ICA studies, the number of ICs is typically set to 20, although it can also be estimated somehow (Calhoun, V. D., Liu, J., Adali, T., 2009. "A review of group ICA for fMRI data and ICA for joint inference of imaging, genetic, and ERP data", Neuroimage, 45, pp S163-S172).

The ICA as a subspace analysis technique has also been widely applied in multivariable data representation with each IC as a basis function for spanning the data subspace. For the subspace data representation based on ICA, different combinations of basis functions (ICs) can be used to capture information of the data with distinctive purposes. For instance, fMRI data's signal to noise ratio can be improved in the subspace data representation by removing ICs corresponding to imaging noise. Similarly, a combination of some ICs, if they are more closely related to the brain function under study, might better capture the brain functional activities from fMRI brain data than combinations of other ICs. In the method proposed in Fan et al. (Y. Fan, Y. Liu, H. Wu, Y. Hao, H. Liu, Z. Liu, T. Jiang, 2011. "Discriminant analysis of functional connectivity patterns on Grassmann manifold", *Neuroimage*, 56, pp. 2058-2067), the ICs of each individual subject's fMRI data were used as basis functions of a linear subspace, referred to as a brain spatial functional connectivity pattern (FCP), and a corresponding pattern similarity a difference measure is proposed. The functional connectivity pattern method may capture the difference between different brain active levels or status.

Many studies have demonstrated that correlation measures between functional signals of two brain regions can capture their functional connectivity information. However, no method has been proposed to simultaneously characterize the spatial functional connectivity pattern from fMRI data based on ICA and correlation measures among time courses (TC) of different ICs, referred to as temporal functional connectivity pattern.

SUMMARY

A subject of the invention is to provide a method for analyzing fMRI brain imaging data.

A method for analyzing fMRI brain data, comprising steps of:
collecting the fMRI data including spatial information and temporal information from subjects;
preprocessing the fMRI data;
computing independent components (ICs) and their corresponding time course for each individual subjects;
constructing an initial functional connectivity pattern;
constructing a classifier based on the functional connectivity pattern; and
applying the classifier to functional connectivity patterns of individual subjects for statistical analysis or diagnosis.

DETAILED DESCRIPTION

The preferred embodiments of this invention is are described in detail with the help of reference to the accompanying drawings. This illustration of the embodiment aims to understand depicts only typical embodiments of the invention and is not therefore to be considered to be limiting of its scope The embodiment captures brain functional information contained in fMRI data of each individual subject with a linear subspace spanned by ICs and their corresponding TCs that are obtained from group ICA of the fMRI data. Such a linear subspace, referred to as a spatial pattern of the brain functional connectivity, could be spanned by different sets of ICs to reflect specific characteristics of the brain function of each individual subject. For the spatial patterns of the brain functional connectivity (they are linear subspaces mathematically), their similarity/difference can be measured in Grassmann manifold. Functional connectivity in time domain between any two ICs can be measured with the correlation coefficient between their TCs. Therefore, the functional connectivity among all ICs in time domain can be characterized by a symmetric matrix with each element measuring the functional connectivity in time domain between two ICs, referred to as a temporal pattern of the brain functional connectivity. The distance/similarity between two temporal patterns of the brain functional connectivity can be measured by Euclidean distance metric between vectors with elements from the upper or lower triangular part of those two symmetric matrices, although other distance/similarity measures for symmetric matrices can be adopted.

Since not all of the ICs computed from fMRI data are relevant to the problem under study, most existing techniques identify informative ICs based on a priori knowledge, novel knowledge may not be discovered. The present invention adopts pattern classification and feature selection strategies to automatically determine the most discriminative FCP by using a forward component selection strategy to optimize the performance of a SVM classifier built on the FCP with the selected ICs. A backward component selection strategy may be used.

The embodiment is directed to a method for automatic identifying the most discriminative functional connectivity pattern (FCP), including both spatial and temporal patterns of the brain functional connectivity, from fMRI data and building a classifier based on the identified most discriminative FCP for pattern classification of fMRI data.

Figure 1:
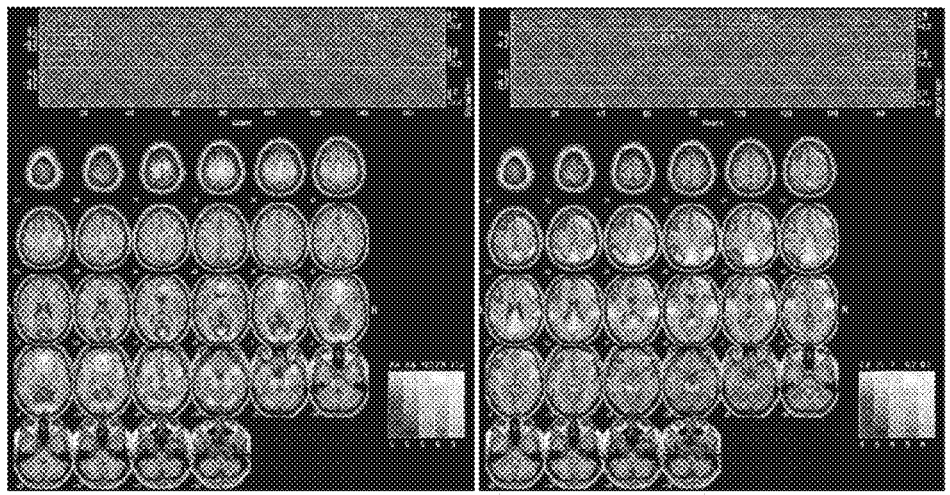
FIG. 1 illustrates 20 spatial ICs (brain functional spatial networks) and their corresponding time courses, computed from resting state fMRI data of a group of cocaine addicts and normal control subjects. The distinctive spatial independent components are shown in different colors.
Figure 1:
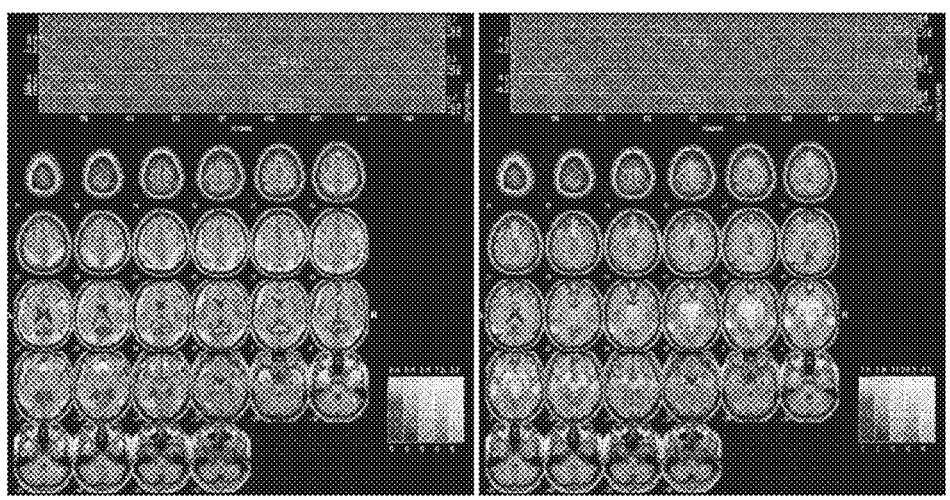

As shown in FIG. 1, from resting state fMRI data of cocaine addicts and normal control subjects, 20 ICs and corresponding TCs are extracted. In particular, image 102, image 104, image 106, and image 108 show 5 ICs and corresponding TCs, respectively. The different colors shown in each image indicates discrete brain functional networks (ICs and corresponding TCs).

Figure 2:
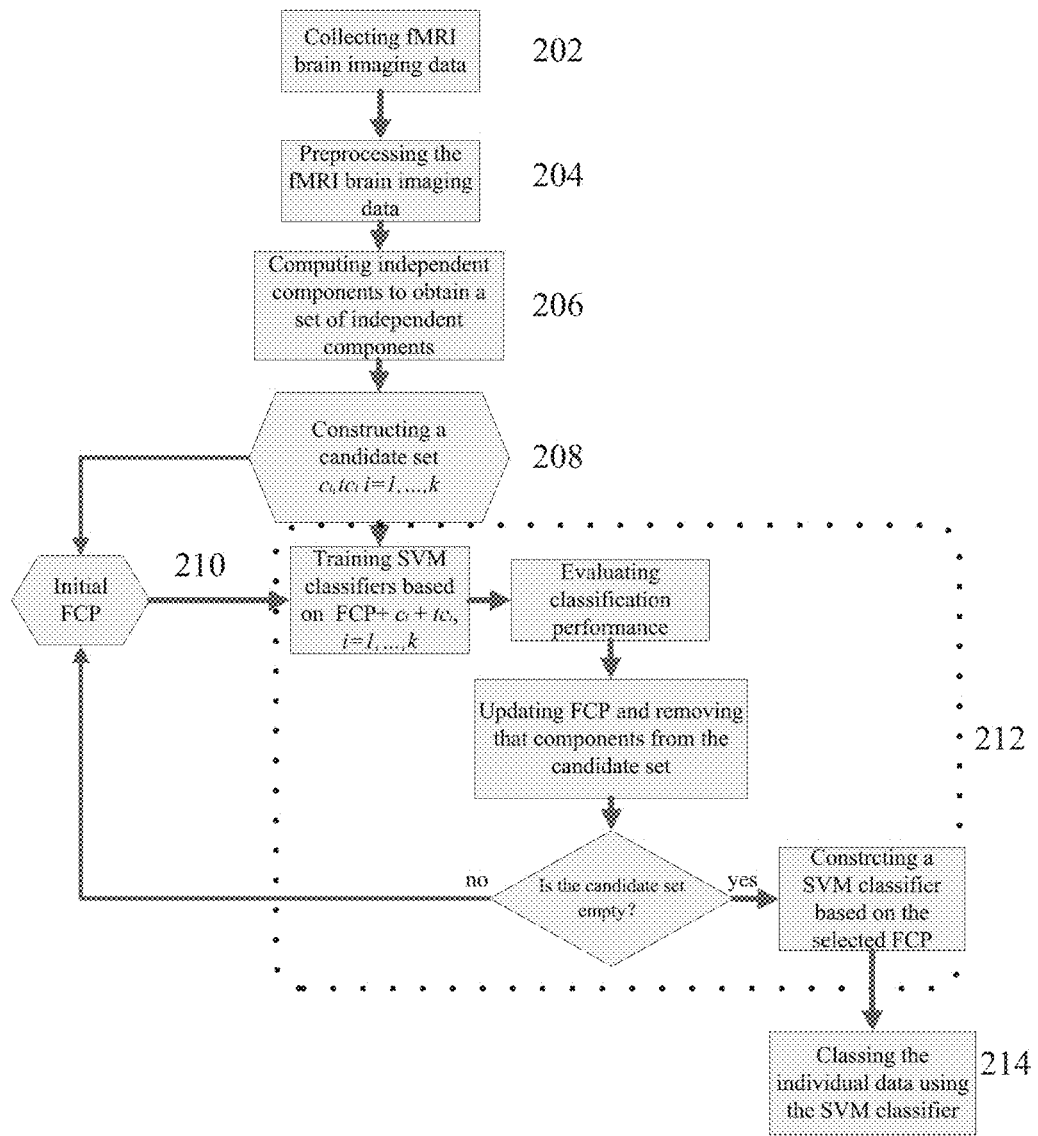
FIG. 2 illustrates a flow chart of a method for identifying the most discriminative functional connectivity pattern.

FIG. 2 illustrates a flow chart of a method for identifying the most discriminative FCP from the extracted ICs and corresponding TCs, and constructing a SVM classifier based on the identified FCP for pattern classification according to an embodiment of the present invention.

At step 202, fMRI brain images are collected from the subjects, and each fMRI brain image is a 4D data set, comprising spatial (3D) and temporal (1D) information. The fMRI brain images can be collected using MRI scanners with Echo Planar Imaging (EPI) sequences. The suggested imaging parameters are: sampling time is in a range of 6-8 minutes, time repeated TR≤2000 ms, slice thickness<5 mm, volumes=240 (480 s). No other special setting is required.

At step 204, the functional MR images are preprocessed. The preprocessing steps may include: slice timing, head movement correction, spatial normalization of functional image to structural image, removing the linear drift, bandpass filtering, spatial normalization to 3 mm MNI space based on structure images, and regressing out the nuisance covariants. The image preprocessing can be implemented as Smith et al., "Advances in Functional and Structural MR image Analysis and Implementation as FSL", NeuroImage 23 (2004), pp. 208-219.

At step 206, ICs and corresponding TCs are computed for each individual subject using a group ICA technique which generates ICs with correspondence across different individuals (Calhoun, V. D., Liu, J., Adali, T., 2009. "A review of group ICA for fMRI data and ICA for joint inference of imaging, genetic, and ERP data", Neuroimage, 45, pp S163-S172). In the group ICA method used, fMRI data from all subjects are firstly temporally concatenated, forming a large 4D fMRI image; then one ICA is performed on the concatenated image, which yields group independent components. To obtain the subject specific ICs and TCs, a back-reconstruction step is implemented by mapping aggregated group independent components to each individual subject.

From each individual's fMRI data, the group ICA method typically yields 20 ICs/TCs. However, the number of ICs to be extracted from fMRI data can also be estimated from the imaging dataset itself using methods described in (Calhoun, V. D., Liu, J., Adali, T., 2009. "A review of group ICA for fMRI data and ICA for joint inference of imaging, genetic, and ERP data", Neuroimage, 45, pp S163-S172).

At step 208, a candidate set of ICs is obtained. The candidate set of ICs can include all ICs extracted at step 206 or only part of them.

At step 210, a starting FCP is obtained. The starting FCP could comprise the ICs identified based on a priori knowledge or could be a void set.

A FCP may include two kinds of information, spatial functional connectivity pattern (FCP_s) and its corresponding temporal functional connectivity pattern (FCP_t). Particularly, FCP_s has been proposed in (Y. Fan, Y. Liu, H. Wu, Y. Hao, H. Liu, Z. Liu, T. Jiang, 2011. "Discriminant analysis of functional connectivity patterns on Grassmann manifold", Neuroimage, 56(4), pp. 2058-2067). The similarity measure between two FCPs is defined as following.

Given the ICs obtained at step 206, denoted by $C=\{c_i|i=1,\ldots,n\}$, and their corresponding TCs, denoted by $TC=\{tc_i|i=1,\ldots,n\}$, a FCP_s is a linear subspace spanned by a subset of IC $$FCP_s = \text{span}(\overline{C}), \overline{C} \subseteq C,$$

where $\overline{C}=\{c_i|i=1,\ldots,k\}$, and its corresponding set of TCs is $\overline{TC}=\{tc_i|i=1,\ldots,k\}$. Its corresponding FCP_t is a vector of Pearson correlation coefficients $$FCP\_t = (r_{j,l} = \text{corr}(tc_j, tc_l)|j=1,\ldots,k, l=1,\ldots,k, j \neq l)$$

where $\text{corr}(tc_j, tc_l)$ is Pearson correlation coefficient between $tc_j$ and $Tc_l$, and could be other correlation measures, such as mutual information. Furthermore, $TC=\{tc_i|i=1,\ldots,n\}$ can be processed with different frequency filters so that correlation measures can be obtained based on filtered time courses at different frequencies.

From a manifold viewpoint, a FCP_s is an element of a Grassmann manifold that is a space of k-dimensional subspaces in an n-dimensional vector space. On a Grassmann manifold, the distance between two FCP_s can be measured by a Riemannian distance metric that is the length of the shortest geodesic connecting these two FCP_s. Among metrics available for measuring the Riemannian distance between elements of the Grassmann manifold, a computational efficient way can be adopted to define a Riemannian distance by utilizing principal angles between two subspaces, which can be computed from the Singular Value Decomposition (SVD) of the dot multiplication of the two subspaces. Given two subspaces $A=(a_1, a_2, \ldots, a_k)$ and $B=(b_1, b_2, \ldots, b_k)$, where $(a_1, a_2, \ldots, a_k)$ and $(b_1, b_2, \ldots, b_k)$ are orthonormal basis vectors for subspaces A and B, respectively, the principal angles between A and B are defined recursively by $$\cos\theta_i = \max_{a_i \in A} \max_{b_i \in B} a_i' b_i = \max_{a_i \in A} \max_{b_i \in B} b_i' a_i, \text{ wherein}$$

$$a_i' a_i = b_i' b_i = 1, a_i' a_j = b_i' b_j = 0, (j=1,\ldots,i-1)$$

$$0 \leq \theta_1 \leq \theta_2 \ldots \leq \theta_k \leq \frac{\pi}{2}$$

A singular value of A'B corresponds to cos θ. Since the ICs of FCPs are not necessarily orthonormal, an orthonormalization has to be implemented before using the SVD procedure to compute the principal angles. From the principal angles, several distance metrics can be derived, for example, a projection metric, which is defined as $$d_p = (\Sigma_{i=1}^k \sin^2\theta_i)^{1/2} = (k - \Sigma_{i=1}^k \cos^2\theta_i)^{1/2},$$

And its corresponding similarity measure between two subspaces can be similarly defined as $$S_p = \left(\frac{1}{k}\sum_{i=1}^k \cos^2\theta_i\right)^{\frac{1}{2}}.$$

Since $FCP_t$ is a vector in Euclidean space, any Euclidean distance metric can be used to measure distance/similarity between two $FCP_{tS}$.

Step 212 is a forward component selection procedure for identifying the most discriminative FCP in conjunction with SVM classification given a set of candidate ICs and their corresponding TCs. The SVM algorithm constructs a maximal margin linear classifier in a high (often infinite) dimensional feature space, by mapping the original features via a kernel function. Plugging the similarity measures of subspaces in the commonly used kernel functions, a kernel function sigmoid for FCPs is defined as $$K(A,B) = \alpha \tan h(\gamma S(A,B)+c)+(1-\alpha)\|A_t-B_t\|,$$

where A and B are two different FCP_s, S(A,B) is a similarity measure between A and B, as defined at step 210, γ and c are two parameters of the kernel function; ||•|| is norm of a vector, $A_t$ and $B_t$ are corresponding FCP_t of A and B, respectively, α is a weighting parameter, ranging from 0 to 1. Since the time courses can be filtered with different frequency filters, $FCP_t$ could be the original time courses, or filtered version with different filters, or their combinations.

Based on the above kernel function, SVM classifiers can be established for FCP_s and FCP_t. Since the ICs have different discriminative power, the discriminative performance of an FCP varies with the ICs. Therefore, a step-wise forward component selection method is used to identify the most discriminative FCP by optimizing its classification performance. As shown in FIG. 1, given a neuroimaging study of brain diseases with fMRI brain images from a set of patients and normal controls, obtaining a candidate set of ICs C=($c_i$|t=1, . . . , k), training examples, $C^j$={$c_i^j$, i=1, . . . , k}, j=1, . . . , n, and their respective class labels $l^j$=+1 or −1, j=1, . . . , n, where j denotes different training examples and i denotes different candidate ICs. Starting with the initial FCP, denoted by $F_0$, we iteratively add more components from C to the FCP one by one. At each iteration step, the incorporated component makes the new FCP more discriminative than others. Specifically, at the $t^{th}$ iteration step, the FCP is updated with $F_i=F_{i-1}+c_i$ and C is updated with C=C/$c_i$, where the SVM classifier built on $F_{i-1}+c_i$ has the best classification performance at the current iteration step. Once C becomes empty after k iteration steps, we choose the FCP with the best classification performance at all the iteration steps as the most discriminative FCP. At each iteration step, the classification performance can be estimated based on the training dataset using leave one out validation or other validation strategies.

At step 214, the SVM classifier built on the most discriminative FCP can be applied to new fMRI brain images for classification. The present invention can be used in neuroimaging studies of brain disorders for identifying FCPs to distinguishing patients from normal individuals.

Figure 3:
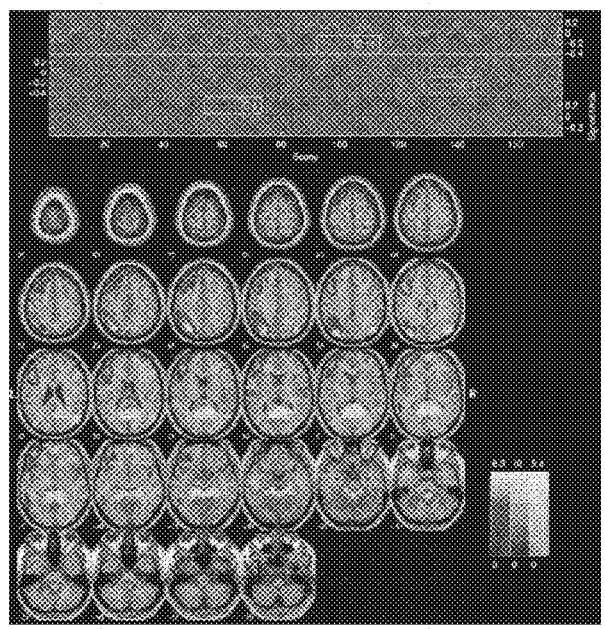
FIG. 3 illustrates the most discriminative functional connectivity pattern for distinguishing cocaine addicts and normal controls, without using a priori knowledge according to an embodiment of the present invention. The distinctive spatial independent components are shown in different colors.

FIG. 3 illustrates the most discriminative FCPs between cocaine addicts and normal controls, identified in a neuroimaging study of cocaine addicts, including ICs and their corresponding TCs. The distinctive ICs are shown in different colors.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention.

What is claimed is:

1. A method for analyzing brain functional magnetic resonance imaging (fMRI) data, comprising steps of:
   collecting the fMRI data including spatial information and temporal information from subjects;
   preprocessing the fMRI data;
   computing independent components (ICs) and their corresponding time course for each individual subjects;
   constructing an initial functional connectivity pattern;
   constructing a classifier based on the functional connectivity pattern; and
   applying the classifier to functional connectivity patterns of individual subjects for statistical analysis or diagnosis,
   wherein the functional connectivity pattern includes a spatial functional connectivity pattern and a corresponding temporal functional connectivity pattern,
   wherein the corresponding temporal functional connectivity pattern includes temporal functional connectivity patterns for one frequency, or temporal functional connectivity patterns for different frequencies, and
   wherein the temporal functional connectivity pattern for one frequency is a vector consisting of elements of correlation coefficients between the temporal functional connectivity patterns for one frequency, or between the temporal functional connectivity patterns for different frequencies.

2. The method of claim 1, wherein the step of preprocessing comprises:
   re-sampling time points so that the time points for collecting all of pixels of a function image corresponding to one time point are the same substantially;
   removing translation and rotation between the functional images collected at different time points due to a head movement by a rigid transformation; and
   applying a spatial normalization to a normal template.

3. The method of claim 1, wherein the step of computing independent components and their corresponding time course for each individual subjects comprises:
   concatenating the fMRI data from all subjects temporally to form a large 4D fMRI image;
   performing an independent component analysis (ICA) the concatenated image to generate group independent components; and
   mapping the group independent components to each individual subject by back-reconstruction to obtain subject specific independent components.

4. The method of claim 1, wherein the time courses are band pass filtered to obtain temporal signals at different frequencies.

5. The method of claim 1, wherein the step of constructing an initial functional connectivity pattern comprise determining portion of the independent components based on a prior knowledge.

6. The method of claim 1, wherein the initial functional connectivity pattern is constructed as an empty set.

7. The method of claim 1, further comprising measuring a similarity or distance between different spatial functional connectivity patterns using a Riemannian distance metric.

8. The method of claim 1, wherein a similarity or a distance between two spatial functional connectivity patterns is described using a principal angle based Riemannian distance metric.

9. The method of claim 1, wherein the similarity or distance between different temporal functional connectivity patterns is measured using Euclidean metrics.

* * * * *